United States Patent [19]

Pera et al.

[11] Patent Number: 5,669,378
[45] Date of Patent: Sep. 23, 1997

[54] INHALING DEVICE

[76] Inventors: Ivo Pera, P.O. Box 9224, Hollywood, Fla. 33084; Francesco Merante, Via della Piaggia, Trevi, Italy, 06039; Marco Cecchini, Via Gigliarelli #110, Perugia, Italy, 06100

[21] Appl. No.: 576,816

[22] Filed: Dec. 21, 1995

[51] Int. Cl.⁶ ............................................. A61M 15/00
[52] U.S. Cl. ........................... 128/203.21; 128/203.15
[58] Field of Search ...................... 128/203.12, 203.15, 128/203.21, 203.23; 604/58

[56] References Cited

U.S. PATENT DOCUMENTS

| | | | |
|---|---|---|---|
| 2,431,649 | 11/1947 | Moats | 128/203.24 |
| 2,442,004 | 5/1948 | Hayward-Butt | 128/203.21 |
| 2,470,296 | 5/1949 | Fields | 128/203.15 |
| 2,470,297 | 5/1949 | Fields | 128/203.15 |
| 2,470,298 | 5/1949 | Fields | 128/203.15 |
| 2,479,002 | 8/1949 | Ceperly | 128/202.21 |
| 2,503,732 | 4/1950 | Heisterkamp | 128/203.15 |
| 2,549,303 | 4/1951 | Friden | 128/203.21 X |
| 2,573,918 | 11/1951 | McCuiston | 128/200.17 |
| 2,579,280 | 12/1951 | Trumbour et al. | 128/203.15 |
| 2,603,215 | 7/1952 | Amow | 128/203.15 |
| 2,603,216 | 7/1952 | Taplin et al. | 128/203.15 |
| 2,702,033 | 2/1955 | Pardeman | 128/202.21 |
| 2,705,007 | 3/1955 | Gerber | 129/203.21 |
| 2,764,154 | 9/1956 | Murai | 128/200.21 |
| 3,807,400 | 4/1974 | Cocozza | 128/203.15 |
| 3,870,046 | 3/1975 | Elliott | 128/203.15 |
| 3,980,074 | 9/1976 | Watt et al. | 128/203.15 |
| 3,991,761 | 11/1976 | Cocozza | 128/203.15 |
| 4,105,027 | 8/1978 | Lundquist | 128/203.15 |
| 4,192,309 | 3/1980 | Poulsen | 128/203.15 |
| 4,206,758 | 6/1980 | Hallworth et al. | 128/203.15 |
| 4,227,522 | 10/1980 | Carris | 128/203.15 |
| 4,338,931 | 7/1982 | Cavazza | 128/203.15 |
| 4,353,365 | 10/1982 | Hallworth et al. | 128/203.15 |
| 4,423,724 | 1/1984 | Young | 128/203.15 |
| 4,569,136 | 2/1986 | Loring | 131/273 |
| 4,627,432 | 12/1986 | Newell et al. | 128/203.15 |
| 4,668,218 | 5/1987 | Virtanen | 604/58 |
| 4,735,217 | 4/1988 | Garth et al. | 131/273 |
| 4,739,754 | 4/1988 | Shaner | 128/203.15 |
| 4,811,731 | 3/1989 | Newell et al. | 128/203.15 |
| 4,841,964 | 6/1989 | Hurka et al. | 128/203.15 |
| 4,846,168 | 7/1989 | Abiko et al. | 128/203.15 |
| 4,884,565 | 12/1989 | Cocozza | 128/203.21 |
| 4,889,114 | 12/1989 | Kladders | 128/203.15 |
| 4,907,583 | 3/1990 | Wetterlin et al. | 128/203.15 |
| 4,993,436 | 2/1991 | Bloom, Jr. | 128/200.21 X |
| 5,031,610 | 7/1991 | Armstrong et al. | 128/200.23 |
| 5,042,472 | 8/1991 | Bunin | 128/203.15 |
| 5,048,514 | 9/1991 | Ramella | 128/203.21 |
| 5,070,870 | 12/1991 | Pearce | 128/203.15 |
| 5,152,284 | 10/1992 | Valentini et al. | 128/203.21 |
| 5,161,524 | 11/1992 | Evans | 128/203.15 |
| 5,176,132 | 1/1993 | Drought et al. | 128/203.15 |
| 5,178,138 | 1/1993 | Walstrom et al. | 128/200.23 |
| 5,203,323 | 4/1993 | Tritle | 128/200.23 |
| 5,205,282 | 4/1993 | Daneshvar | 128/203.26 |
| 5,207,217 | 5/1993 | Cocozza et al. | 128/203.21 |
| 5,239,991 | 8/1993 | Chawla et al. | 128/203.15 |
| 5,239,992 | 8/1993 | Bougamont et al. | 128/203.15 |
| 5,239,993 | 8/1993 | Evans | 128/203.15 |

(List continued on next page.)

FOREIGN PATENT DOCUMENTS 2 142 246   1/1985   United Kingdom ............. 128/203.21

*Primary Examiner*—V. Millin
*Assistant Examiner*—Eric P. Raciti

[57] ABSTRACT

A monodose disposable inhaling device is disclosed which is suitable for delivery, via the respiratory tract, therapeutic medication, which includes among its objects and advantages increased convenience in medication with dry medicaments in powder form, especially with respect to accuracy of dosage and accurate placement of the drug. In one embodiment the inhaler device generally consists of a body member having a delivery portion constructed integral with a housing portion, a button member, a spring member and a spring and capsule support member. Additionally, a screen member can be disposed within the body member at the intersection of the delivery portion and the housing portion.

19 Claims, 7 Drawing Sheets

U.S. PATENT DOCUMENTS

| | | | |
|---|---|---|---|
| 5,243,970 | 9/1993 | Ambrosio et al. | 128/203.15 |
| 5,263,475 | 11/1993 | Altermatt et al. | 128/203.15 |
| 5,287,850 | 2/1994 | Haber et al. | 128/203.21 |
| 5,295,479 | 3/1994 | Lankinen | 128/203.15 |
| 5,301,666 | 4/1994 | Lerk et al. | 128/203.15 |
| 5,320,095 | 6/1994 | Nijkerk et al. | 128/203.15 |
| 5,320,714 | 6/1994 | Brendel | 128/203.15 |
| 5,327,883 | 7/1994 | Williams et al. | 128/203.12 |
| 5,337,740 | 8/1994 | Armstrong et al. | 128/203.12 |
| 5,341,800 | 8/1994 | Clark et al. | 128/203.15 |
| 5,349,947 | 9/1994 | Newhouse et al. | 128/203.21 |
| 5,351,683 | 10/1994 | Chiesi et al. | 128/203.12 |
| 5,372,128 | 12/1994 | Haber et al. | 128/203.21 |
| 5,379,763 | 1/1995 | Martin | 128/203.15 |
| 5,383,850 | 1/1995 | Schwab et al. | 604/58 |
| 5,388,572 | 2/1995 | Mulhauser et al. | 128/203.15 |
| 5,388,573 | 2/1995 | Mulhauser et al. | 128/203.15 |
| 5,388,574 | 2/1995 | Ingebrethsen | 128/203.17 |
| 5,394,868 | 3/1995 | Ambrosio et al. | 128/203.15 |
| 5,415,162 | 5/1995 | Casper et al. | 128/203.12 |
| 5,435,301 | 7/1995 | Herold et al. | 128/203.15 |

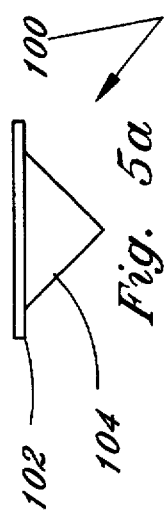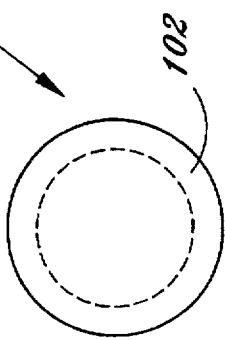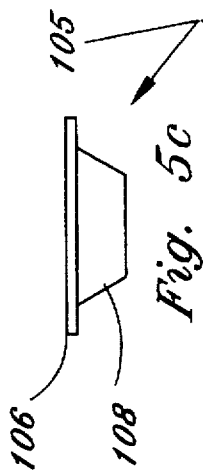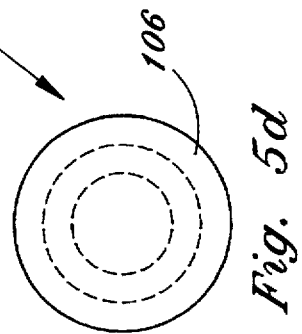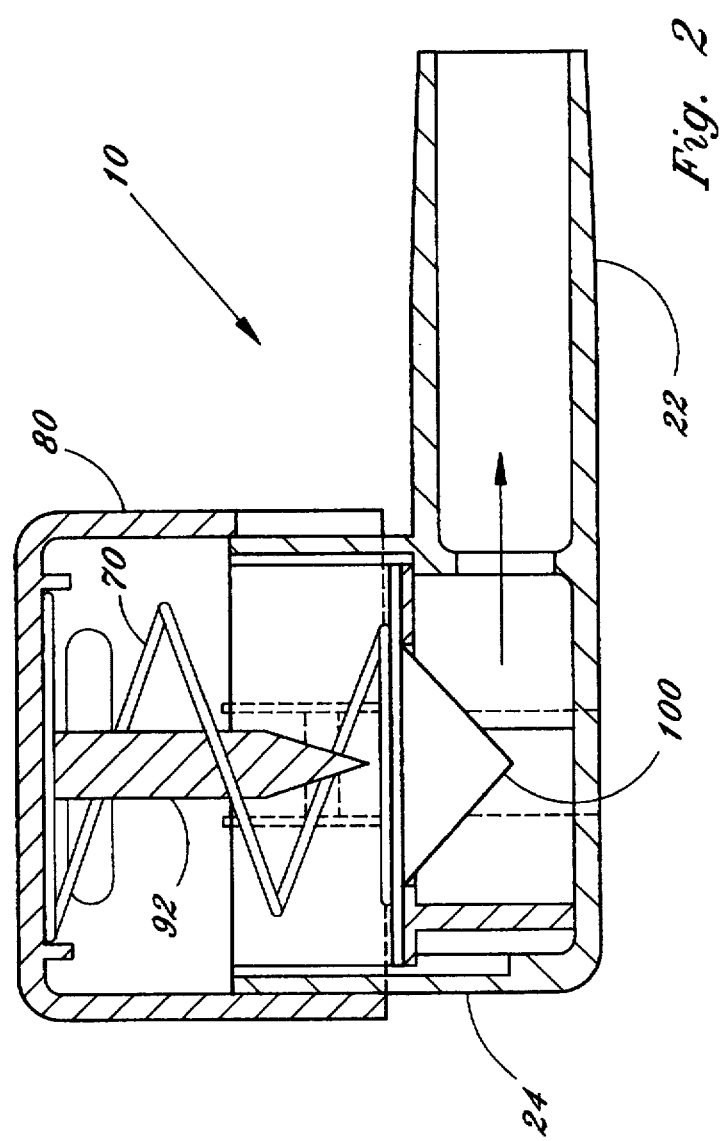

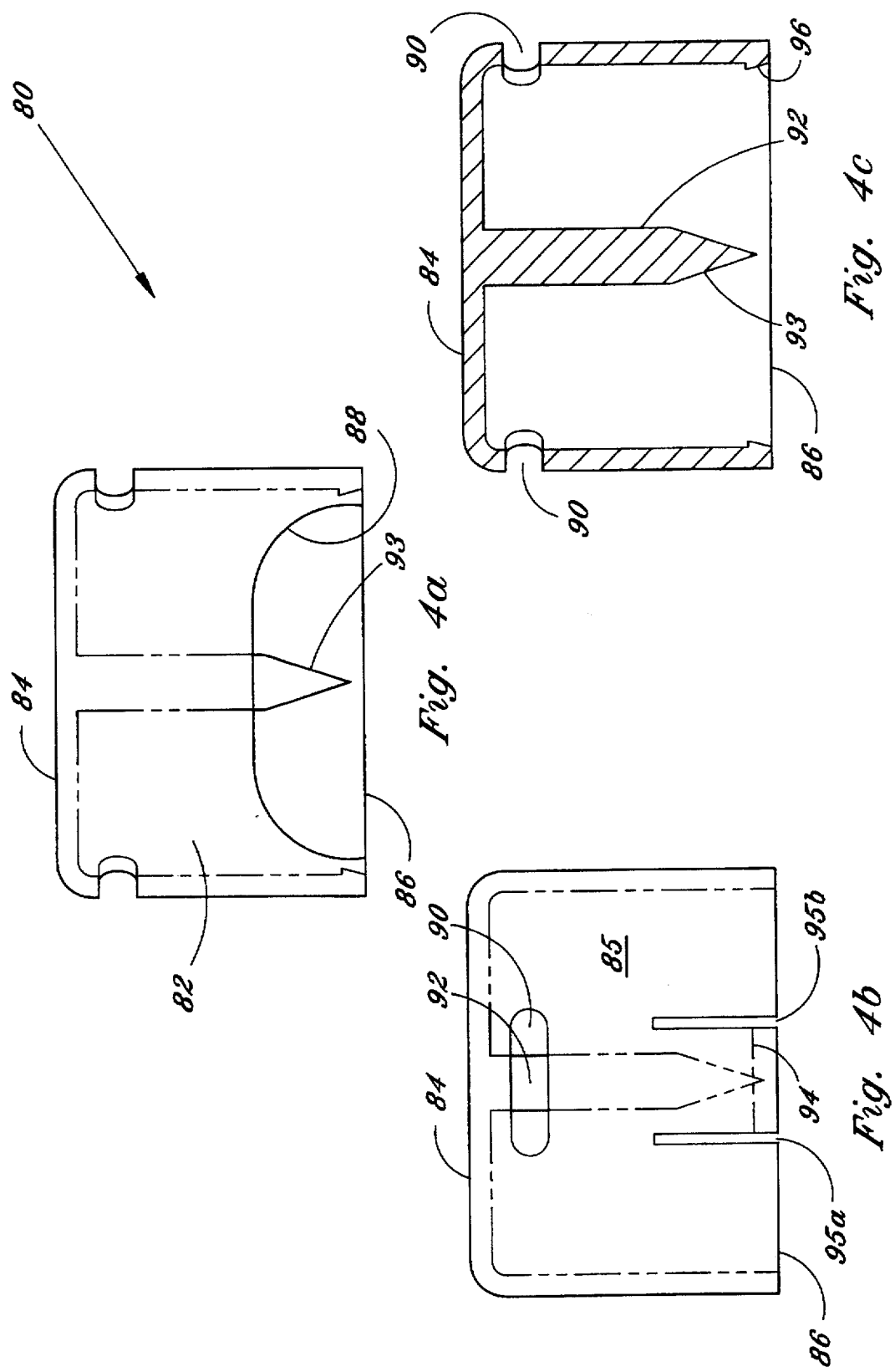

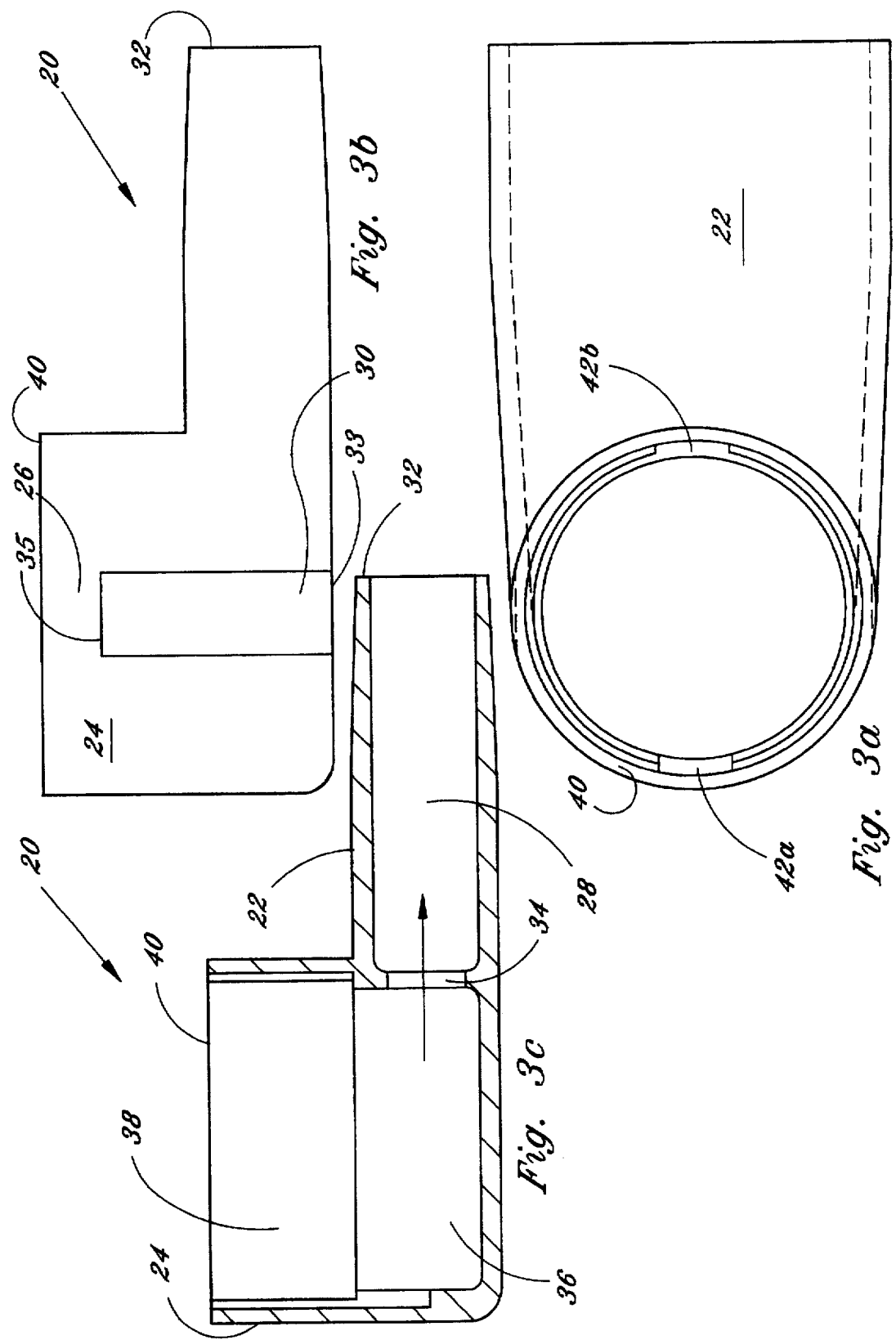

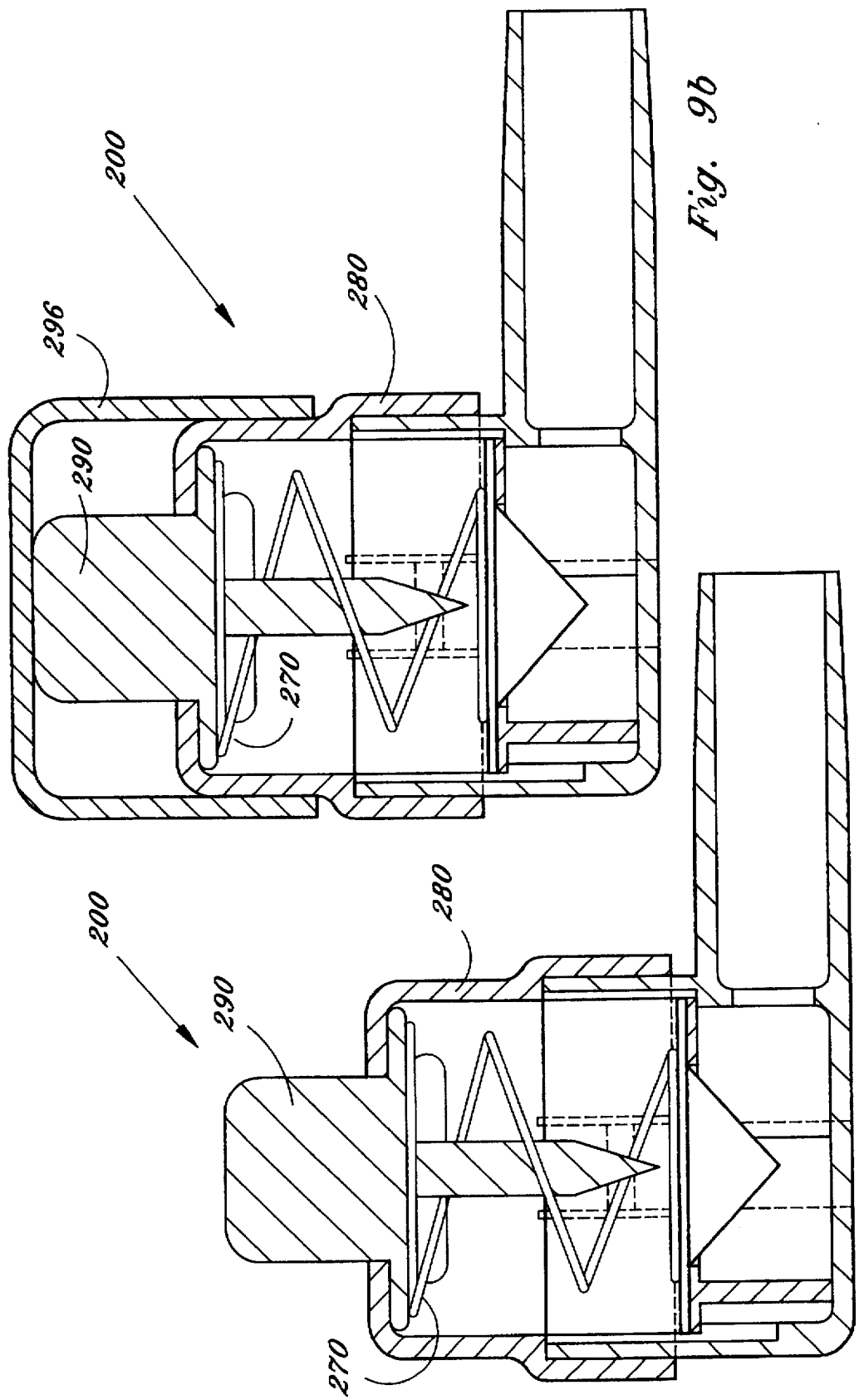

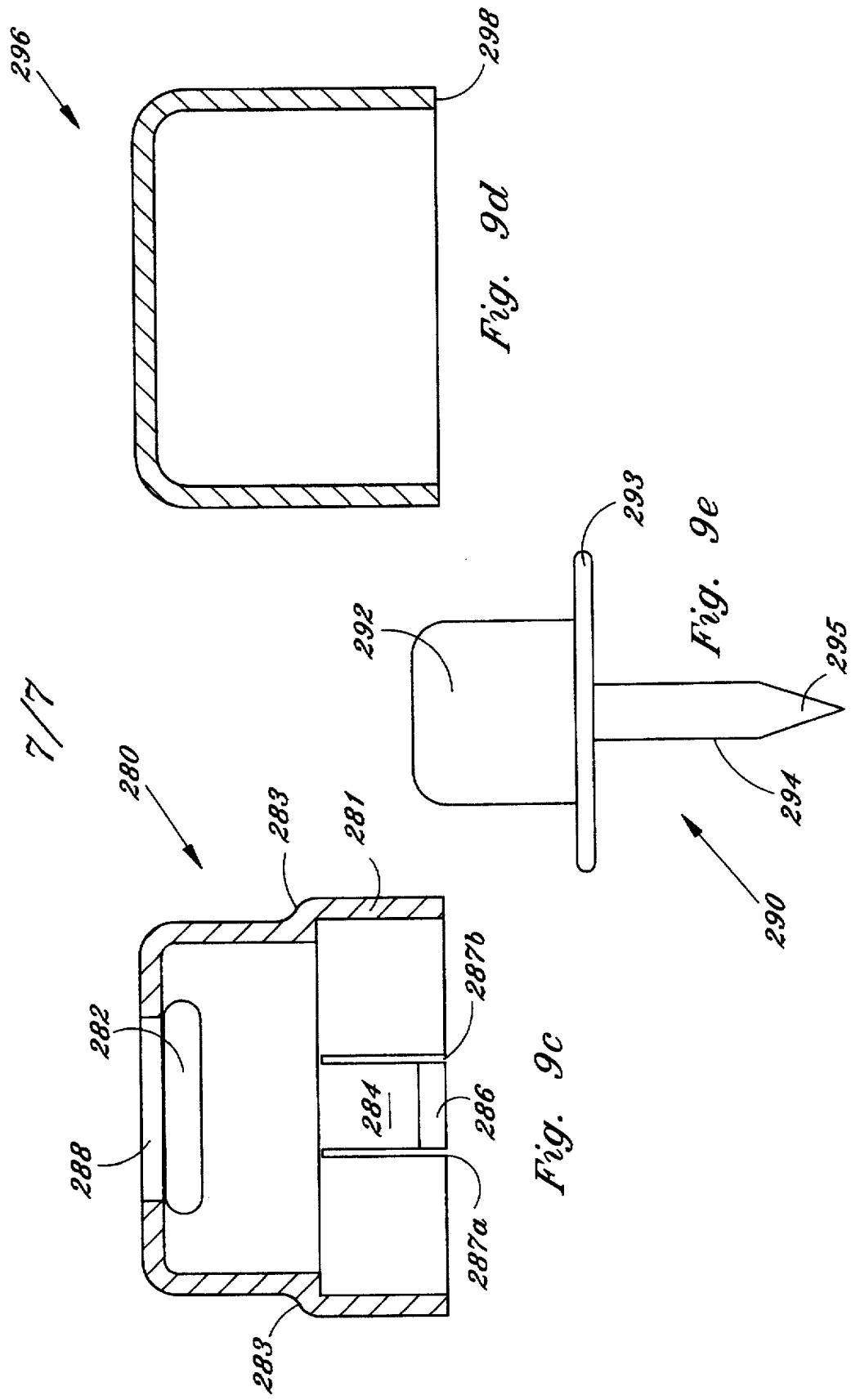

INHALING DEVICE

BACKGROUND OF THE INVENTION

1. Field of the Invention

The present invention relates generally to inhalers, and more particularly to a monodose disposable inhaling device.

2. Description of the Prior Art

The lung is considered to be one of the more effective, noninvasive routes of administration to the systemic circulation. A number of powdered medications can be used to treat a variety of conditions that accompany many different diseases. Conditions requiring an inhaling device, particularly in such therapy where it can be administered to a patient on a program of home care, include (1) infection, (2) mucosal edema, (3) tenacious secretions, foam buildup, (5) bronchospasms, and (6) loss of compliance. Furthermore, infections are often accompanied with one or more of these identified conditions.

Inhalation of powdered medicaments by inertial devices is a complex and important issue. Conventional dry powder inhalers deliver their dose of drug on the breath of the patient. The conventional dry powder inhaler has a characteristic resistance to laden airflow rate, therefore, the pressure drop, and by inference the volumetric flow through these systems, will vary. The general properties given rise to errors in these inhalers when dispensing proper medicaments are specific directional and velocity characteristics, including, but not limited to, instability and concentration of the mass of particles administered in a unit volume of air. Additionally, in a definitive clinical setting the patient's inspiratory flow can vary significantly.

Several devices have been developed for the administration of micronized powders of relatively potent drugs. The Norisodrine Sulfate Aerohaler Cartridge (Abbott) is an example of such devices. With this device the inhalation by the patient causes a small ball to strike a cartridge containing the necessary drug. The force of the ball shakes the proper amount of the powder free, permitting its inhalation. Other devices include the SPINHALER (Fisons) and the TURBO-HALER (Astra), which are propeller-driven devices designed to deposit a mixture of lactose and micronized cromolyn sodium into the lung. Additional devices includes the ROTAHALER, BECLODISK, DISKHALER, VENTO-DISKAND DISKUS, all developed by the Glaxo company, and are used for the administration of powdered drugs to the respiratory tract. These devices have proven to cumbersome, complicated and relatively expensive. As such, the single use of these devices is not practical.

Consequently, these multidose devices are reused, despite reasons of hygiene and the difficulty of keeping the mouthpiece of the devices clean. Some of these devices are provided with special brushes for cleaning the mechanism. However, it becomes readily apparent that such brushes are ineffective for correctly sanitizing the multidose device for reuse. It would be proper and more convenient and sanitary to provide an inhaler which is disposable after a single use.

Additionally, current inhaling devices often result in problems of obtaining a proper mixture with the air during the transmission of the medication to the breathing portions of the body, thereby affecting efficiency of the medicinal mixture. A further problem often found with present inhaling devices is that the medication is not completely drawn out of the inhaling device resulting in undesirable caking and collection of films within the inhaler device, as well as the patient not receiving the desired dosage of medication. Thus, output from present inhaling devices, is highly variable, as well as inefficient.

It is generally estimated that with conventional inhalers, only about ten percent (10%) of the inhaler drug actually reaches the lungs of the patient, with the remaining ninety percent (90%) being deposited on the lining of the mouth and throat. As the desired relief to the patient from the use of the conventional inhaler often does not occur, the patient commonly quickly presses for another does of the drug. Accordingly, using these inhalers is often likely, under certain circumstances, to cause serious unpleasant side effects to the patient, including but not limited to, mild irritation in the patient's throat area, dysphonia, nausea, jitterness, indigestion, gastic reflux, insomnia, thrush, hoarsehess, coughing, oropharyngeal candidosis, etc.

Patients, who are often elderly, often find it difficult to understand the complexities of the present inhaling devices, including the multi-disk methods of loading and administering the dry powdered medicament. This frustration often causes a refusal to utilize the device by the patient, even after the patient has ultimately been successful with administration of the medicament. Surprisingly, this resistance and difficulty is often found even among doctors themselves, if nothing else because of the time required to explain the procedure to the patient. Instructional materials, usually enclosed with the medicine, though clear, are nevertheless only theoretical. In synthesis everything about present inhaling devices is seen as complex and difficult and is thus at least resisted, if not outright refused. Accordingly, patients have, and will continue to, express the various difficulties they have found with current inhaling devices, which include, but are not limited to, comprehensibility, repetition, reliability and especially the necessity of continuous elucidation regarding the mode of use for powdered inhalators.

The problems described above, frequently result in the premature abandoning of the medicinal formulation, even by the more sensitive and careful subjects, possibly returning to spray devices. Despite its apparent simplicity of use and rapidity, spray devices are liable to constant errors, both on part of the patient and on the part of medical staff. Coordinating the manual spray and respiratory actions is somewhat difficult, resulting in the spray ending up on the patient's tongue and not in the desired lower respiratory airways. Thus, the patient may not even realized that medicine had been transmitted by the spray device. This often leads to repeated dosages by the patient, with their possible cumulative side effects, as well as other problems.

Many useful medicaments, especially penicillin and related antibiotics, are subject to substantial or, in some instances, complete alteration by stomach juices when administered orally. Different patients vary widely in the condition of the alimentary canal to the extent to which oral dosages will be impaired in effectiveness. In fact, the same patient will react differently to the same dosage at different times, because the condition of the patient's alimentary canal varies from time to time.

On this account, precision in treatment has only been attainable in the past with oral dosages supplemented by checking blood samples to ascertain how much medicament has found its way into the blood stream, or by parenteral administration.

Powdered medicaments administered by inhalation are not frequently used for delivery into the systemic circulation, due to various factors that contribute to erratic or difficult-to-achieve blood levels. Whether or not the powder drugs reaches and is retained in the pulmonary alveoli depends critically upon particle size (particles greater than 1 micromillimeter (um) in diameter tend to settle in the bronchioles and bronchi, whereas particles less than 0.6 micromillimeter (um) fail to settle and are mainly exhaled). With pharmacopeia, particle size is of major importance in the administration of this type of preparation. Various types of mechanical devices are currently used in conjunction with inhalers and are reported in accompanying literature that the optimum particle size for penetration into the pulmonary cavity is of the of ½ to 7 micromillimeters (um).

All of the problems described above for current inhaling devices has caused dry powder preparation to be relatively unknown, even in the hospital environment, where the priority in potency and dignity of the "pill" medicine still exists, as it does outside the hospital.

Thus, what is needed in the art is a inhaling devices which is relatively easy to use and low in cost, to allow the device to be disposed of after a single use, for the hygiene purposes. Being used for a single dosage of medicine, also will aid in the ease of operation for the inhaling devices, thus eliminating loading and reloading of medications, as well the difficulties in effectively cleaning such device. It is to the effective elimination of the above described problems with current inhaling devices that the present invention is directed.

SUMMARY OF THE INVENTION

The present invention generally provides a monodose disposable inhaling device for dispensing a single dose of powdered medicaments into the respiratory tract. In one embodiment the inhaling device generally consists of a body member having a delivery portion and a housing portion, a button member, a spring member and a spring and capsule support member. The button member includes a post member having a sharp pointed puncturing end. Additionally, screen means can be disposed within the body member at the intersection of the delivery portion and the housing portion.

In use, with all of the above parts properly attached, a capsule member, having the desired medicaments (preferably in a dry powder form) stored within the capsule, is disposed within a powder receiving area of the housing portion. When the patient or user requires the desired medicaments, he or she places the outer end of the delivery portion into his or her mouth and presses the button member downward. Preferably, the user breathes-in while pressing the button member downward. The pressing of the button member downward causes a sharp pointed end of the post member to extend through the capsule and into the powder receiving area, thus, puncturing the capsule to release the stored dry powdered medicament into the powder receiving area. The breathing-in by the user causes the released medicaments to relatively quickly enter the delivery portion and ultimately the lungs of the patient. The screen means is sized to prevent the capsule member or pieces of the capsule member from entering into the delivery portion and possibly the user.

As the inhaling device is relatively inexpensive, the user preferably disposes of the device after its single use. Thus, the user is not bothered with removing the punctured capsule member and replacing it with a new capsule member having the desired medicaments inside. Further, the user does not have to worry about properly cleaning the inhaling device after each use.

The present invention inhaler follows the logic of a single and exact dose of medicine disposed within a conventional capsule member, including, but not limited to, a small aluminum foil bag. The capsule member, containing the medicine therein, is disposed within the housing portion of the body member, which is preferably constructed from plastic, or other appropriate material which can also be biodegradable, and suitable for inhalation, due to its conformation. The medicine disposed within the bag is made available to the patient by the simple pressing of a button member while the patient simultaneously breathes inward. The pressing of the button member by the patient causes a post member associated with the button to puncture the bag which delivers the powdered medicine to the central lumen (lower area of housing portion) for delivery. The medicine is then subject to a vortex of air created by the particular conformation of the internal channel (defined by the housing portion and button member) of the inhaler, thus ensuring an adequate dispersion and micronization of the powder. Additionally, the delivery channel (delivery portion of the body member) can be somewhat flare outward or tapered, to ensure a correct opening of the patient's lips.

The entrance nozzle of the air is supplied by a special valve which ensures the one way flow of the air and eliminates the possibility of mistaken actions before or during the inhalation of the powdered medicament. The present invention inhaler greatly scatters the powder medicament, as compared to prior art inhalers, leaving a relatively very low rate of powdered drug remaining in the inhaler. The present invention inhaler can be manufactured by means of injection moldings well known in the art, thereby affecting substantial cost reduction in manufacturing the device without adversely affecting the medicament administration inhalation.

To use the inhaler of the present invention the patient breathes in, in a simple, substantially normal way. The energy of air flowing through the inhaler is utilized to deliver into the lining a single dose of powdered medicaments. This charge of energy is delivered quickly, relatively shortly after inhalation begins, and finds its way to its desired location (respiratory tract). Thus, the inhaler itself and the body passages first receiving the stream of air are thoroughly swept and scavenged with pure air during a major portion of the breathing-in process. Administration of the medicament in this fashion, contributes to deep penetration of the medicament, and eliminates the need to pulverize or micronize the medicament into true smoke. As such, the use of larger particle of medicament, tends to increase the reliability with which a uniform fraction of the medicament will pass through the body passages first receiving the air stream, without getting caught on the moist walls of the body passage.

The drug can be delivered into the alveoli of the lungs. The alveolar and vascular epithelial membranes are quite permeable and blood flow is abundant. Thus a relatively very large surface for adsorption is provided and use of the present invention allows for virtually rapid absorption of the powdered medicaments.

The monodose disposable inhaling device can be used in respiratory therapy, as well as for other diseases, through the topical administration of medications through the mucosal linings of the tracheo-bronchial tree and the lungs. The monodose disposable inhaling device of the present invention allows the user to effectively and smoothly inhale the powdered medicaments into the pulmonary tract, by the simple inspiration of air.

The use of the monodose disposable inhaling device of the present invention through the respiratory tract may provide an efficient means of administering dry powder medicaments such as vasoconstrictors, antihistaminics, antispamodics, antipeptics, antibronchiolitis, B2-stimulants-corticosteroids, antivirals, antifungals, antioxidants, antileukotrienes, antiallergens, antibiotics, human proteins, peptides, etc. These medicaments will generally require a smaller dosage then necessary if such medicaments were given systemically.

The present invention can be utilized to properly dispense powdered medicinals, as well as for other applications with potentially enormous benefits which can be hypothesized for other substances such as cortisteroids, for vaccines which are currently being developed for the treatment of allergies, for antibiotics used in cyclical and prophylactic treatment particularly of chronic bronchitis and chronic bronchial pathologies with recurrent infections (mucoviscidosis, immune deficiency syndrome, AIDS, etc.).

The present invention also provides for reduction of oral mycosis, commonly associated with spray devices, which deposit the medicinals in the area of the tongue and oropharynx, due to the backwards direction of the spray itself. The present invention eliminates such as it is disposable, thus, providing for optimal micronisation. Use of the inhaler of the present invention allows for dispensing of powdered medicaments available in the form of fine powders which allows for a high concentration of the medicament to reach the respiratory tract for effective therapeutic effect.

Furthermore, as the present invention is relatively easy to operate, patients are less prone to become frustrated when taking their prescribed medicants, resulting in a greater percentage of patients completing the therapy and receiving proper dosages, as well as reducing hospital time required for receiving the therapy or instructions on how to self-administer the prescribed medicants.

The present invention can be utilized with antibiotics, steroids and other difficult soluble compounds. Problems associated with the formulation of these drugs include agglomeration, caking, particle-size growth and often clogging, which are eliminated by the use of the present invention.

The invention makes possible to dispense any type of powdered drugs which are at all times completely under the control of the user. Thus, the present invention inhaler provides a simple and convenient means of dispensing powdered drugs, and is capable of extremely wide applications.

It is an object of the present invention to provide an inhaling device which allows a single dose of powdered medicaments to be disposed within the respiratory tract.

It is another object of the present invention to provide an inhaling device which is disposable.

It is still another object of the present invention to provide an inhaling device which will properly dispense powdered medicants.

It is even still another object of the present invention to provide an inhaling device which permits the correct dosage of medicant to be administered to the patient.

It is yet another object of the present invention to provide an inhaling device which is easy to use and relatively inexpensive.

It is a further object of the present invention to provide an inhaling device which allows for relatively lower production costs.

It is an even further object of the present invention to provide an inhaling device which permits a better perception of results by a prescribing doctor or physician, thus, allowing for increase of confidence in the medicinal formulation.

It is even still another object of the present invention to provide an inhaling device which is extremely simple, fool-proof, and allows a user to easily achieve maximum control of his or her health.

It is an additional object of the present invention to provide an inhaling device which will maintain its characteristics for relatively long periods of time, such that if a considerable amount of time elapses between the original manufacture of the device and its utilization, the therapeutic efficacy of the drug will remain comparatively undiminished.

In accordance with these and other objects which will become apparent hereinafter, the instant invention will now be described with particular reference to the accompanying drawings.

BRIEF DESCRIPTION OF THE DRAWINGS

The invention may be better understood by reference to the drawings in which:

FIG. 2 is a front sectional view of the invention shown in FIG. 1;

FIG. 3a ia a top view of a first embodiment body member of the present invention;

FIG. 3b is a front elevational view of the body member of FIG. 3a;

FIG. 3c is a front sectional view of the body member of FIG. 3a;

FIG. 4a is a side elevational view of a button member of the present invention;

FIG. 4b is a front elevational view of the button member of FIG. 4a;

FIG. 4c is a side sectional view of the button member of FIG. 4a;

FIG. 5a is a front elevational view of a first embodiment capsule member in accordance with the present invention;

FIG. 5b is a top view of the capsule member of FIG. 5a;

FIG. 5c is a front elevational view of a second embodiment capsule member in accordance with the present invention;

FIG. 5d is a top view of the capsule member of FIG. 5c;

FIG. 6b is a top view of the body member of FIG. 6a;

FIG. 9a is a front sectional view of an alternative button member embodiment for the present invention;

FIG. 9b is a front sectional view of an alternative button member embodiment for the present invention also including a protective cover member;

FIG. 9c is a front sectional view of a first cover member of the alternative button embodiment illustrated in either FIG. 9a or FIG. 9b;

FIG. 9d is a front sectional view of the protective cover member of the alternative button embodiment illustrated in FIG. 9b; and FIG. 9e is front elevational view of the button and puncturing member of the alternative button embodiment illustrated in either FIG. 9a or FIG. 9b.

DETAILED DESCRIPTION OF THE PRESENT INVENTION

Figure 1:
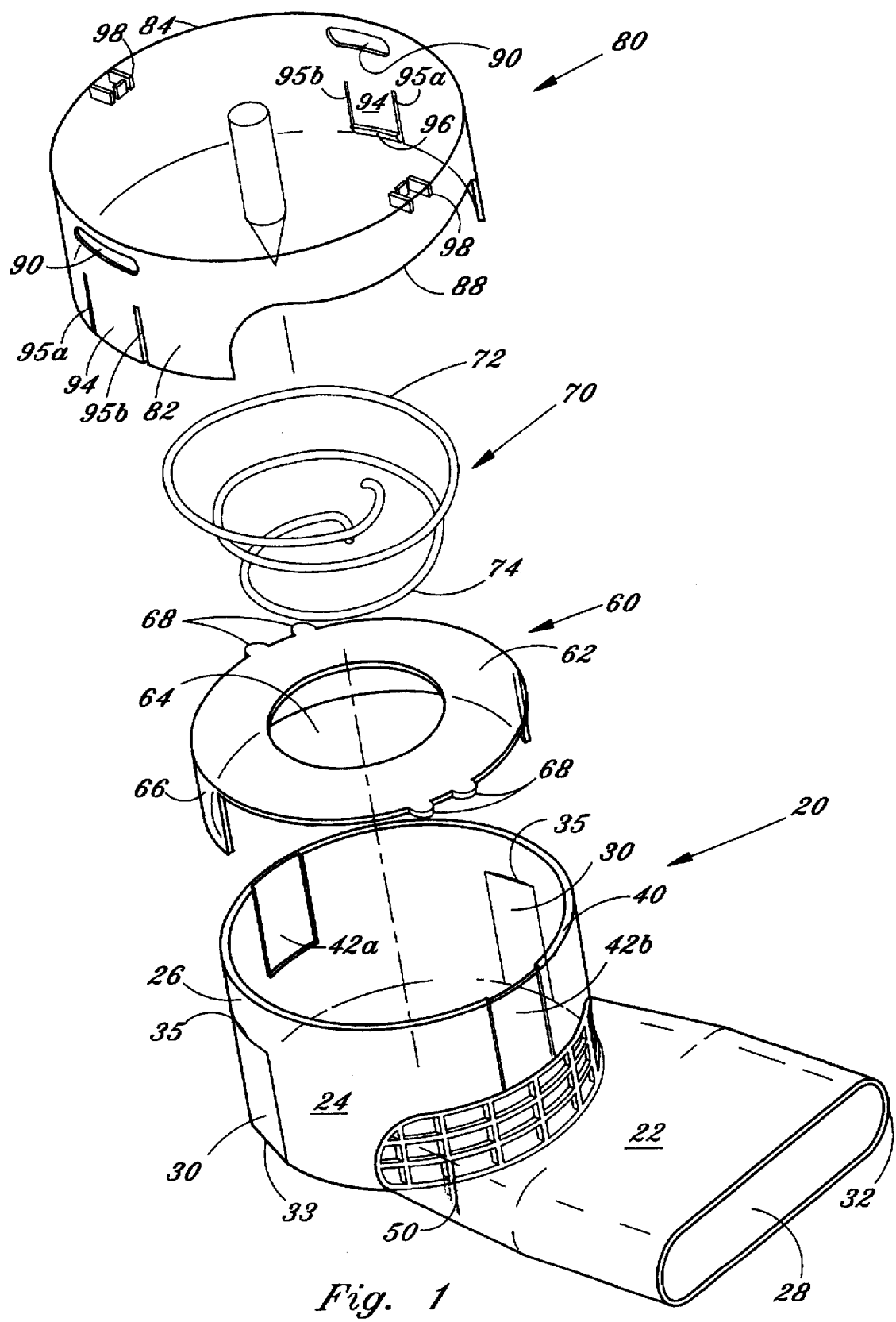
FIG. 1 is an exploded perspective view of a first embodiment of the present invention.

As seen in FIGS. 1 through 4, the first embodiment of a monodose disposable inhaling device is shown and generally designated as reference numeral 10. Inhaler 10 generally consists of a body member 20 having a delivery portion 22 and a housing portion 24, a button member 80, a spring member 70 and a spring and capsule support member 60. Additionally, a screen means 50 can be disposed within body member 20 at the intersection of delivery portion 22 and housing portion 24. Screen means 50 can be associated with an outer grid member, as is known in the art.

As stated above, body member 20 includes a delivery portion 22 and a housing portion 24. Preferably, delivery portion 22 and housing portion 24 are constructed integral. Delivery portion 22 has a first open end 32 and a second open end 34. A medicant passageway 28 is defined by delivery portion 22 extending from first end 32 to second end 34. Preferably, delivery portion 22 and, thus, passageway 28, taper outward from second end 34 to first end 32, to ensure a correct opening of the patient's lips.

Housing portion 24 includes a bottom section defining a powder receiving area 36 and a top section defining a portion of a spring receiving area 38. Housing portion 24 also includes an open top end 40. The bottom section of housing portion 24 defines an aperture to allow passageway 28 of delivery portion 22 to communicate with housing portion 24 at powder receiving area 36. A screen means 50 having a grill member 52 can be disposed within the aperture defined by the bottom section of housing portion 24. In lieu of screen means 50, a plurality of apertures can be formed in housing portion adjacent the intersection of the second end of delivery portion 22 and housing portion 24, to allow delivery passageway 28 to communicate with powder receiving area 36.

Housing portion 24 also includes a wall member 26 having an outer slot or groove 30 which can extend upward and deeper within wall member 26 from its first end 33 to its second end 35 to define a button retaining means at second end 35. A button retaining means can be a wall member formed at second end 35 by the increase in depth of slot 30 from first end 33 to second end 35. Wall member 26 also defines inner grooves or slots 42a and 42b, which extend downward from top end 40 along a substantial portion of wall member 26 to provide air entrances into powder receiving area 36.

Spring and capsule support member 60 includes a spring and capsule resting portion 62 having an aperture 64 extending therethrough and a positioning member 66 extending downward from resting portion 62. Support member 60 is disposed within housing portion 24. Preferably, positioning member 66 abuts the bottom of powder receiving area 36 when support member 60 is disposed within housing portion 24. Resting portion 62 also defines the top of powder receiving area 36. Thus, positioning member 66 should be at least slightly greater in height than a capsule 100 or 105 containing the powdered medicament(s), to assure that capsule 100 or 105 (FIGS. 5a–5d) properly depends from support member 60 into powder receiving area 36.

To further assure that positioning member 66 does not block or partially block the communication between delivery passageway 28 and powder receiving area 36, at least one protrusion 68 depends outward from resting portion 62. When placing support member 60 within housing portion 24, protrusions 68 are aligned within inner groove 42a and travel along groove 42a until positioning member 66 abuts the bottom of powder receiving area 36. Protrusions 68 are preferably disposed adjacent the center of positioning member 66 to ensure proper placement of support member 60 within housing portion 24. Additionally, protrusions 68 also help to prevent the shifting or horizontal movement of support member 60 during the operation of inhaler 10, which could also block or partially block the communication between delivery passageway 28 and powder receiving area 36. Preferably, two protrusions 68 are provided. Though protrusions 68 are disposed within groove 42a, sufficient area is still provided for air to travel into receiving area 36 through groove 42a.

Though, not preferred, in lieu support member 60, an inner ledge member (not shown), can be formed integral within wall member 26. The inner ledge member, thus, defines the top of powder receiving area 36 and the bottom of spring receiving area 38 and also provides the resting area for spring means 70 and capsule 100 or 105. The ledge member should be formed high enough along wall member 26 to allow sufficient room in powder receiving area 36 for the receipt of various sizes of capsules. A pair of gaps in the ledge member should also be provided to allow grooves 42a and 42b to continue into receiving area 36.

After support member 60 is properly disposed within housing portion 24, a capsule member, such as, but not limited to, either capsule 100 or 105, is properly disposed within housing portion 24. Capsule 100 or 105 can be a conventional capsule and is preferably constructed from aluminum foil or a plastic film. Medicament storing area 104 or 108 of capsule 100 or 105, respectively, is inserted through aperture 64 of support member 60 until respective capsule ledge member 102 or 106 abuts resting area 62. At this point capsule 100 or 105 is properly positioned within housing portion 24 and spring means 70 is disposed within housing portion within spring receiving area 38. The desired dry powder medicament is stored within capsule 100 or 105 within storing area 104 or 108, respectively. Preferably, the powder medicament will be of a particle size in accordance with the range described above.

The bottom of spring receiving area 38 is defined by resting portion 62 while the top of spring receiving area 38 is defined by button member 80 when it is attached to housing portion 24, discussed in detail below. Spring means, can be a conventional spring, and has a first end 72 which abuts capsule 100 or 105 and a second end 74 which abuts an inner portion of button member 80, also discussed in detail below.

After spring means 70 is properly disposed, button member 80 is attached to housing portion 24 by the mating of at least one ear member 94 with corresponding grooves 30 in wall member 26. Preferably, two ear members 94 and two corresponding grooves are provided. A protrusion 96 depends inward from ear member 94. Ear members 94 can be formed by creating slots 95a and 95b within wall member 82 of button member 80. Button member 80 includes a closed top end 84 and an open bottom end 86. Wall member 82 and closed top end 84 define the top section of spring receiving area 38. The inner diameter of button member 80 is slightly larger then the outer diameter of housing portion 24, for the receipt of a top section of housing portion 24 within button member 80 when button member 80 is attached to housing portion 24.

Button member 80 also defines a cutout 88 at a bottom area of wall member 82 which is sized to receipt a portion of delivery member 22 when button member is pressed, discussed in detail below. Furthermore, at least one, and preferably two apertures 90 extending through wall member 82 near top end 84 can be provided. Apertures 90 provide turbulence and increase velocity during the depression of button member 80, discussed further below. Thus, holes 90 improve the turbulent flow of air inside the chamber (housing portion 24) of body member 20. This improved turbulent flow of air is also provided by grooves 42a and 42b disposed within wall member 26.

Button member 80 can also be provided with spring retaining members 98. End 72 of spring member 70 can be retained between retaining member 98, to prevent spring member 70 from shifting out of position. With the use of retaining members 98, end 72 of spring 70 can be attached to button member 80 prior to disposing spring 70 into housing portion 24. After end 72 is attached to button member 80, end 74 of spring member 70 is inserted within housing portion 24 and button member 80 is attached to housing portion 24 relatively, quick thereafter, if not simultaneously.

Button member 80 is also provided with a post member 92 protruding downward within the top of spring receiving area 38 defined by wall member 82 and top end 84. Preferably, post 92 is formed integral with button member 80 at the inner surface of closed top end 84. Post member 92 includes a sharp pointed end 93 for puncturing a capsule, such as capsule 100 or 105, disposed within powder receiving area 36 during the use of inhaler 10, discussed below. Post member 92 also extends through spring means 70 when button member 80 is properly attached to housing portion 24.

Spring means 70 maintains button member 80 in a first upward position to help prevent post member 92 from inadvertently puncturing capsule 100 or 105 containing the powdered medicament which is disposed within powder receiving area 36 of housing portion 24, prior to the pressing of button member 80. In this upward position, protrusions 96 abut second end 35 of groove 30, which acts as a stop means, and maintains the attachment of button member 80 to housing portion 24.

In use, with all of the above parts properly attached, capsule member 100 or 105, having the desired medicaments (preferably in a dry powder form) stored within area 104 or 108 of capsule 100 or 105, respectively, is disposed within powder receiving area 36 as discussed above. When the patient or user requires the desired medicaments, he or she places end 32 of delivery portion 22 in his or her mouth and presses button member 80 downward. Preferably, the user breathes-in while pressing button member 80 downward. The pressing of button member 80 downward provides a turbulent air flow within housing portion 24 and causes pointed end 93 to extend through capsule 100 or 105 and aperture 64 of support member 60 and into powder receiving area 36, puncturing capsule member 100 or 105 to release the stored dry powdered medicament into powder receiving area 36.

The breathing-in by the user causes the released medicaments to relatively quickly enter passageway 28 of delivery portion 22 and ultimately the respiratory tract of the patient. Screen means 50 is sized to prevent the capsule member or pieces of the capsule member from entering into passageway 28 and possibly the user. Preferably, button member 80 is depressed until cutout 88 abuts its adjacent portion of delivery portion 22. This abutted relationship also defines the maximum downward position button member 80 can be pressed.

As inhaling device 10 is relatively inexpensive, the user preferably disposes of device 10 after its single use. Thus, the user is not bothered with removing the punctured capsule member and replacing it with a new capsule member having the desired medicaments inside. Further, the user does not have to worry about properly cleaning inhaling device 10 after each use.

However, though not preferred, inhaling device 10 can be reused, as button member 80 can be removably attached to housing portion 24. In such event, after use, button member 80 and spring means 70 are removed. The punctured capsule is removed and if support member 60 is provided it can also be removed for easier cleaning of inhaler 10. After support 60 is once again properly disposed within housing portion 24, a new capsule member is then disposed, as described above, preferably after device 10 has been properly cleaned. Spring means 70 and button member 80 are then properly positioned and reattached.

Preferably, device 10 is instructed from plastic, however, other conventional materials, though not preferred, are within the scope of the invention. Additionally, it is also preferred, though not required, that body member 20, support member 60 and button member 80 be transparent. In such embodiment, it will be readily apparent to the user whether his or her breathing actions have removed all of the released dry powder of medicaments from receiving area 36. It is also preferred that housing portion 24, support member 60 and button member 80 be substantially circular in shape.

Figure 6A:
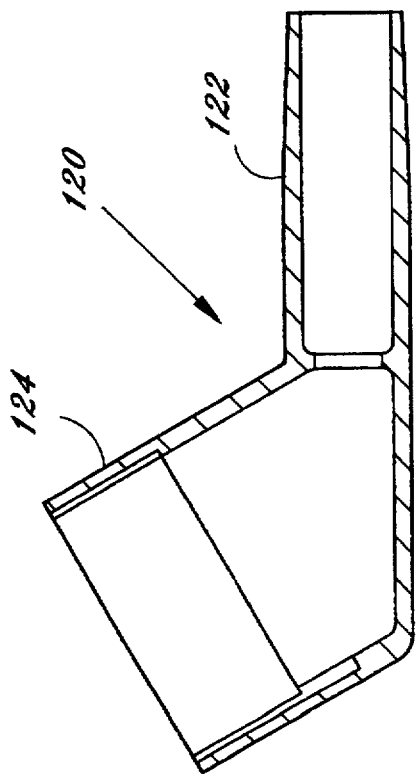
FIG. 6a is a front sectional view of a first alternative body member embodiment of the present invention.
Figure 6B:
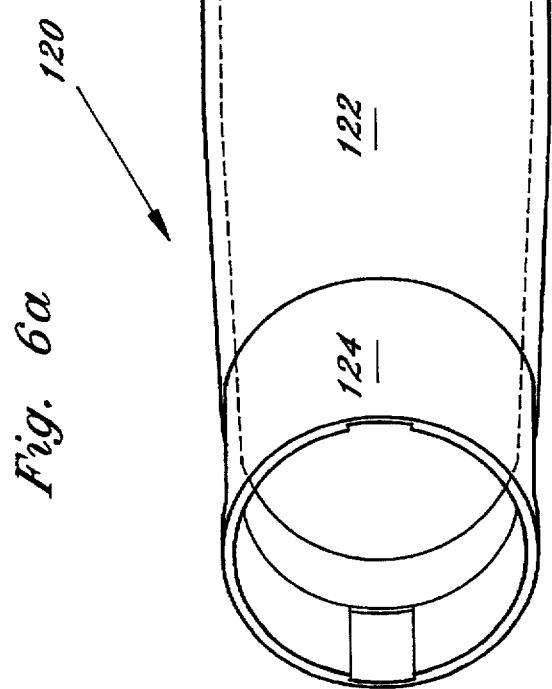

FIGS. 6a and 6b illustrate an inhaling device having alternative body member embodiment 120. In this embodiment, delivery portion 122 is similar to delivery portion 22, but housing portion 124 is constructed integral with delivery portion 122 at an angle, preferably from, but not limited to, forty-five (45°) to sixty (60°) degrees, instead of perpendicular, as housing portion 24 is constructed integral with delivery portion 22 for inhaling device 10.

Angled housing portion 124 allows for greater velocity and more speed during the releasing of the powdered medicaments, thus, allowing the powdered medicaments to reach the user quicker due to the improvement of the turbulent flow of air within housing portion 124. This embodiment can be utilized with small children, elderly patients, or other individuals who may not be able to breath-in at the same strength as an healthy adult. All other parts of the inhaling device are similar to like parts for inhaling device 10.

FIGS. 9a–9e illustrate an inhaling device 200 having an alternative embodiment for its button member. In lieu of button member 80 disclosed above, inhaler 200 includes a first cover member 280 having a wall member 281. Ear members 284, having respective protrusions 286 are formed by slots 287a and 287b in wall member 281, similar to ear member 94 and protrusion 96. Apertures 282 are provided within wall member 281, similar to apertures 90. An additional aperture 288 is provided in top end 289 which is sized to receive a pressing portion 292 of button 290, discussed below. First cover member 280 can also be provided with a ledge 283.

Button member 290 includes pressing portion 292, lip or intermediate portion 293 and a post member 294 having a pointed end 295 which depends downward from lip portion 293. Post member 294 is similar to post 92. The diameter of pressing portion 292 is slightly smaller than the diameter of aperture 288. Prior to attaching first cover member 280 to housing portion 224 (which is similar to the attachment of button member 80 to housing portion 24), pressing portion is inserted through aperture 288 until intermediate portion 293 is abutting the inner surface of top end 289. Once first cover member 280 is attached to housing portion 224, spring 270 maintains button 290 in an upward position. To utilize inhaler 200, the user simply presses the protruding pressing portion 292 and inhaler 200 operates as described above for inhaler 10.

A protective cover member 296 can be provided and is attached to first cover member 280 to prevent inadvertent pressing of button member 292. The inner diameter of second cover member 296 is slightly larger than the diameter of the inserted portion of first cover member 280. When attached to first cover member 280, a lower end 298 of second cover member 296 rest upon ledge 283. When the user wishes to use inhaler 200, he or she simply removes cover member 296 and the presses button 290 as discussed above.

All parts of inhaler 200 not discussed are similar to parts previously discussed for inhaler 10 or 110. Furthermore, the alternative button embodiment discussed for inhaler 200, with or without second cover member 296 can also be utilized with angled inhaler 110.

Figure 7:
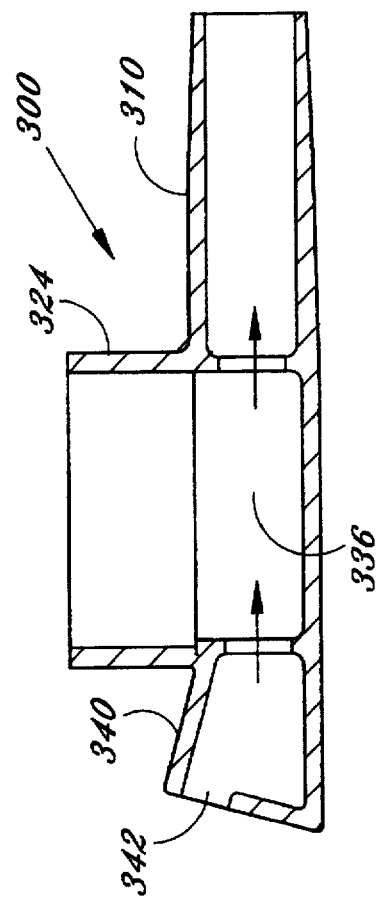
FIG. 7 is a front sectional view of a second alternative body member embodiment of the present invention.
Figure 8:
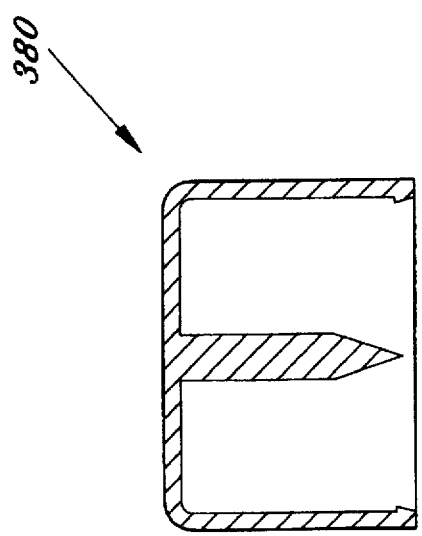
FIG. 8 is a front sectional view of a button member used in conjunction with the body member illustrated in FIG. 7.

An additional alternative body member embodiment of the present invention is shown in FIGS. 7 and 8 and is generally designated as body member 300. Body member includes a delivery portion 310 communicating with a housing portion 324 and a button member 380. A screen means can also be provided. Preferably, delivery portion 310 and housing portion 324 are constructed integral. Delivery portion 310 includes an open first end and a second end. Delivery portion 310 also defines a passageway extending from its first end to its second end. Housing portion 324 includes a powder receiving area 336.

In this embodiment, grooves 42a and 42b and apertures 90, discussed above, are eliminated and an air entrance way into powder receiving area 336 is provided by a flanged portion 340 associated with the bottom of housing portion 324. Flange portion 340 includes an aperture 342 which allows ambient air to enter within powder receiving area 336. Flanged portion 340 can be angled to facilitate air flow into powder receiving area 336 during use of inhaling device 300.

Besides, the addition of flanged portion 340, and the elimination of grooves 42a and 42b and apertures 90, this embodiment of the present invention, is structurally similar to any of the other embodiments, described above, and also functions similarly, as well as being operated by the user similarly.

All of the embodiments of the present invention provide for a proper mixture of air with the medication during the transmission of the medication to the breathing portions of the body, thereby increasing the efficiency of the medicinal mixture.

It should be recognized that the size of the various components are illustrated larger in the drawings, for purposes of clarity, than the individual pieces of the inhaling devices are in real life.

The various embodiments of the monodose disposable inhaling device of the present invention efficiently dispenses powdered medicinals through the respiratory tract, which provides the following advantages:

(1) easy to use, relieving the patient of mental tension and anxiety regarding the mode of administration and the immediate check of the completed operation;

(2) placebo effect advantage for the patient deriving from the psychological tranquillisation due to the simplicity of the method of administration, this being particularly relevant with elderly patients;

(3) guarantee of the correct dosage and achievement of the therapeutic result, not only to benefit illiterate and elderly patients, but children too;

(4) optimization of the dispensing method due to its simplicity, dependability, reliability, and relatively low manufacturing costs;

(5) inhaling device is, preferably, discarded following the administration of the contained drug, thus, avoiding hygiene problems of multidose devices which after the first time of their use can be contaminated with bacterias and are easily soiled and subject to blockage;

(6) elimination of various doctors and physicians reservations, which currently are not in favor of preserving extensively the use of powdered drugs through the use of inhalers;

(7) avoids the necessity of patient education and extensive patient training in how to use inhaling device, particularly with chronic therapies (where inhalers often require more than one step to performed by the patient);

(8) efficacious and ready to be used with most powdered medicines, including, but not limited to, antibiotics, mucollitics, antioxidants, hormone, vaccines, corticosteroids, etc. (which currently are not commonly prescribed via inhalations due to lack of efficient devices and cultural instruction;

(9) elimination of the confusion between long-acting and ready-to-use medicines;

(10) resolution of the problem of patient co-operation; and

(11) eye appealing and very small, thus, not an inconvenience for the patient to carry the inhaler;

(12) eliminates manual problems, maintenance problems, hygiene problems, comprehension problems, mistaken use and psychological conditions, while providing an uncomplicated and efficient method for delivering powdered medicaments via the respiratory tract.

As is shown in the drawings and described above, the concept in question is carried out through the use of a disposable administration devices which can be adapted in their dimensions, external aspects, and internal and external configuration. However, all of the devices follow the logic of a single and exact dose of medicine in a container made of plastic, or other appropriate material which can also be biodegradable, and suitable for inhalation, due to its conformation.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An inhaling device for delivering powdered medicaments to a patient, the powdered medicaments disposed within a capsule member, said inhaling device comprising:
   a body member having a delivery portion and a medicament housing portion, said delivery portion in communication with said medicament housing portion, the capsule member containing the powdered medicaments being disposed within said housing portion; and
   means for releasing the powdered medicament into the delivery portion of said body member, said means for releasing including a button member releasably attached to said housing portion, said button member including a post member, said post member having a pointed first end, wherein pressing said button member causes the pointed first end of said post member to puncture the capsule member causing the powdered medicaments to be released within the delivery portion of said body member, said post member depending from approximately the center of said button member.

2. The inhaling device of claim 1 wherein said means for releasing further including a spring member disposed within said housing portion above said capsule member, a first end of said spring member abutting at least a portion of said button member, wherein said spring member maintaining said button member in an uppermost position when said button member is not pressed to prevent said pointed first end of said post member from inadvertently puncturing the capsule member.

3. A monodose disposable inhaling device for delivering powdered medicaments to the respiratory tract of a patient, the powdered medicaments disposed within a capsule member, comprising:

a body member including a delivery portion and a medicament housing portion, said delivery portion having an open first end and a second end and defining a passageway therethrough, said medicament housing portion having a closed bottom end, an open top end, and a wall member, said wall member having an inner surface and an outer surface;

a seat member disposed within said housing portion, said seat member including a spring resting portion, said spring resting portion having an aperture extending therethrough, a portion of the wall member, the closed bottom end and said seat member defining a capsule receiving area for disposal therein of the capsule containing the powdered medicaments, said delivery portion communicating with the capsule receiving area;

a spring member having a first end and a second end, the first end of said spring member resting upon an upper surface area of said spring resting portion; and a button member removably attached to the wall member of said housing, the second end of said spring member abutting said button member, said button member also including a post member having a relatively pointed first end.

4. The monodose disposable inhaling device of claim 3 wherein said housing portion and said button member are substantially circular in shape, wherein said button member having an inner diameter which is slightly larger than an outer diameter of said housing portion.

5. The monodose disposable inhaling device of claim 3 wherein the spring member is compressed and the pointed end of the post member extends through the aperture in said spring resting portion when said button member is pressed.

6. The monodose disposable inhaling device of claim 3 further including a screen means for preventing the capsule or portions of the capsule from leaving the capsule receiving area of said housing when said capsule is punctured, said screen means disposed at the second end of said delivery portion where said delivery portion communicates with said capsule receiving area.

7. The monodose disposable inhaling device of claim 3 wherein said button member including a wall member and a top end, the wall member of said button member having a cutout portion disposed at a bottom end of said button member, said cutout portion shaped to receive an associated portion of said delivery portion when said button member is pressed thus allowing said button member to be pressed a greater distance, wherein said button member is fully depressed when said associated portion of said delivery portion is fully received within said cutout portion.

8. The monodose disposable inhaling device of claim 7 wherein an inner surface of the wall member of said button member having at least one flange member protruding inward for mating with an associated slot member disposed on the outer surface of the wall member of said housing member, said slot member having a stop means disposed at its first end, said flange member traveling along its associated slot member when said button member is depressed, said flanged member resting against said stop means when said button member is not depressed to removably retain said button member to said housing member.

9. The monodose disposable inhaling device of claim 8 wherein the mating of said at least one flanged member with its associated slot member properly aligns and attaches said button member to said housing member.

10. A monodose disposable inhaling device for delivering powdered medicaments to the respiratory tract of a patient, the powdered medicaments disposed within a capsule member, comprising:

a body member including a delivery portion and a medicament housing portion, said delivery portion having an open first end and a second end and defining a passageway therethrough, said medicament housing portion having a closed bottom end and an open top end, said medicament housing portion also containing a ledge member extending inward from an inner surface of a wall member of said housing, said wall member also having an outer surface, a portion of the wall member, the closed bottom end and the ledge member defining a capsule receiving area for disposal therein of the capsule containing the powdered medicaments, the second end of said delivery portion communicating with the capsule receiving area;

a spring member having a first end and a second end, the first end of said spring member resting upon an upper surface area of said ledge member; and a button member removably attached to the wall member of said housing, the second end of said spring member abutting said button member, said button member also including a post member having a relatively pointed first end.

11. The monodose disposable inhaling device of claim 10 wherein said delivery portion tapers outward from said second end to said first end.

12. The monodose disposable inhaling device of claim 10 wherein the spring member is compressed and the pointed end of the post member extends through the aperture defined by said ledge member when said button member is pressed.

13. The monodose disposable inhaling device of claim 10 further including a screen means for preventing the capsule or portions of the capsule from leaving the capsule receiving area of said housing when said capsule is punctured, said screen means disposed at the second end of said delivery portion where said delivery portion communicates with said capsule receiving area.

14. The monodose disposable inhaling device of claim 10 wherein said housing portion and said button member are substantially circular in shape.

15. The monodose disposable inhaling device of claim 14 wherein said button member having an inner diameter which is slightly larger than an outer diameter of said housing portion.

16. The monodose disposable inhaling device of claim 10 wherein said button member including a wall member and a top end, the wall member of said button member having at least one aperture disposed therein near the top end and a cutout portion disposed at a bottom end of said button member, said cutout portion shaped to receive an associated portion of said delivery portion when said button member is pressed thus allowing said button member to be pressed a greater distance, wherein said button member is fully depressed when said associated portion of said delivery portion is fully received within said cutout portion.

17. The monodose disposable inhaling device of claim 16 wherein an inner surface of the wall member of said button member having at least one flange member protruding inward for mating with an associated slot member disposed on the outer surface of the wall member of said housing member, said slot member having a stop means disposed at its first end, said flange member traveling along its associated slot member when said button member is depressed, said flanged member resting against said stop means when said button member is not depressed to removably retain said button member to said housing member.

18. The monodose disposable inhaling device of claim 17 wherein said button member having two flange members and said housing member having two slot members.

19. The monodose disposable inhaling device of claim 18 wherein the mating of said flanged members with their respective slot members properly aligns and attaches said button member to said housing member.

* * * * *